United States Patent
Li et al.

(10) Patent No.: US 12,134,789 B2
(45) Date of Patent: Nov. 5, 2024

(54) CONSTRUCTION METHOD AND APPLICATIONS OF GLYCOSYLTRANSFERASE BS-YJIC MUTANT

(71) Applicant: Northwest university, Xi'an (CN)

(72) Inventors: Weina Li, Xi'an (CN); Daidi Fan, Xi'an (CN); Chenhui Zhu, Xi'an (CN)

(73) Assignee: Northwest university, Xi'an (CN)

( * ) Notice: Subject to any disclaimer, the term of this patent is extended or adjusted under 35 U.S.C. 154(b) by 0 days.

(21) Appl. No.: 18/614,748

(22) Filed: Mar. 25, 2024

(65) Prior Publication Data

US 2024/0318153 A1   Sep. 26, 2024

(30) Foreign Application Priority Data

Mar. 25, 2023   (CN) .......................... 202310299778.6

(51) Int. Cl.
*C12N 9/10* (2006.01)
*C12N 15/70* (2006.01)
*C12P 17/06* (2006.01)

(52) U.S. Cl.
CPC ............ *C12N 9/1051* (2013.01); *C12N 15/70* (2013.01); *C12P 17/06* (2013.01); *C12Y 204/01* (2013.01)

(58) Field of Classification Search
CPC ....... C12N 9/1051; C12N 15/70; C12P 17/06; C12Y 204/01
See application file for complete search history.

(56) References Cited

PUBLICATIONS

Liu et al. Structural and biochemical studies of the glycosyltransferase Bs-YjiC from Bacillus subtilis. International Journal of Biological Macromolecules (2021), 166: 806-817. (Year: 2021).*
Zhao et al. Single site mutations of glycosyltransferase with improved activity and regioselectivity for directed biosynthesis of unnatural protopanaxatriol-type ginsenoside product. Molecular Catalysis (2021), 515: 111937. (Year: 2021).*
Guo et al. Enhancement of thermal stability of Bacillus subtilis 168 glycosyltransferase YjiC based on PoPMuSiC algorithm and its catalytic conversion of rare ginsenoside PPD. Process Biochemistry (2023), 132:1-12. (Year: 2023).*
Northwest University (Applicant), Supplemental amendment of CN202310299778.6, w/ replacement claims (allowed), Aug. 14, 2023.
CNIPA, Notification to grant patent right for invention in CN202310299778.6, Aug. 21, 2023.

* cited by examiner

*Primary Examiner* — Iqbal H Chowdhury
(74) *Attorney, Agent, or Firm* — Hemisphere Law, PLLC; Zhigang Ma

(57) ABSTRACT

A glycosyltransferase BS-YjiC mutant, a construction method and an application thereof provided, relating to the field of genetic engineering technologies. The glycosyltransferase BS-YjiC mutant is obtained by performing site-directed mutation on amino acids at the $125^{th}$, $178^{th}$, $313^{th}$, $125^{th}$ and $178^{th}$, or $125^{th}$ and $313^{th}$ positions of a wild-type glycosyltransferase BS-YjiC with the amino acid sequence as shown in SEQ ID NO: 1. Compared with the wild-type glycosyltransferase BS-YjiC, the glycosyltransferase BS-YjiC mutant is more suitable for catalyzing protopanaxadiol (PPD) to generate rare ginsenosides F12 and Rh2, which is more conducive to the flexibility of the production process.

1 Claim, 2 Drawing Sheets

Specification includes a Sequence Listing.

SEQUENCE LISTING

```
Sequence total quantity: 8
SEQ ID NO: 1                    moltype = AA   length = 392
FEATURE                         Location/Qualifiers
source                          1..392
                                mol_type = protein
                                organism = unidentified
SEQUENCE: 1
MKKYHISMIN IPAYGHVNPT LALVEKLCEK GHRVTYATTE EFAPAVQQAG GEALIYHTSL    60
NIDPKQIREM MEKNDAPLSL LKESLSILPQ LEELYKDDQP DLIIYDFVAL AGKLFAEKLN   120
VPVIKLCSSY AQNESFQLGN EDMLKKIREA EAEFKAYLEQ EKLPAVSFEQ LAVPEALNIV   180
FMPKSFQIQH ETFDDRFCFV GPSLGERKEK ESLLIDKDDR PLMLISLGTA FNAWPEFYKM   240
CIKAFRDSSW QVIMSVGKTI DPESLEDIPA NFTIRQSVPQ LEVLEKADLF ISHGGMNSTM   300
EAMNAGVPLV VIPQMYEQEL TANRVDELGL GVYLPKEEVT VSSLQEAVQA VSSDQELLSR   360
VKNMQKDVKE AGGAERAAAE IEAFMKKSAV PQ                                392

SEQ ID NO: 2                    moltype = DNA   length = 1176
FEATURE                         Location/Qualifiers
source                          1..1176
                                mol_type = other DNA
                                organism = unidentified
SEQUENCE: 2
atgaaaaaat atcatattag catgattaac attccggcgt atggccatgt gaacccgacc    60
ctggcgctgg tggaaaaact gtgcgaaaaa ggccatcgcg tgacctatgc gaccaccgaa   120
gaatttgcgc cggcggtgca gcaggcgggc ggcgaagcgc tgatttatca taccagcctg   180
aacattgatc cgaaacagat tcgcgaaatg atggaaaaaa acgatgcgcc gctgagcctg   240
ctgaaagaaa gcctgagcat tctgccgcag ctggaagaac tgtataaaga tgatcagccg   300
gatctgatta tttatgattt tgtggcgctg gcgggcaaac tgtttgcgga aaaactgaac   360
gtgccggtga ttaaactgtg cagcagctat cgcgcagaacg aaagctttca gctgggcaac   420
gaagatatgc tgaaaaaaat tcgcgaagcg gaagcggaat ttaaagcgta tctggaacag   480
gaaaaactgc cggcggtgag ctttgaacag ctggcggtgc cggaagcgct gaacattgtg   540
tttatgccga aaagctttca gattcagcat gaaacctttg atgatcgctt ttgctttgtg   600
ggcccgagcc tgggcgaacg caaagaaaaa gaaagcctgc tgattgataa agatgatcgc   660
ccgctgatgc tgattagcct gggcaccgcg tttaacgcgt ggccggaatt ttataaaatg   720
tgcattaaag cgtttcgcga tagcagctgg caggtgatta tgagcgtggg caaaaccatt   780
gatccggaaa gcctggaaga tattccggcg aactttacca ttcgcagag cgtgccgcag   840
ctggaagtgc tggaaaaagc ggatctgttt attagccatg gcggcatgaa cagcaccatg   900
gaagcgatga acgcgggcgt gccgctggtg gtgattccgc agatgtatga acaggaactg   960
accgcgaacc gcgtggatga actgggcctg ggcgtgtatc tgccgaaaga agaagtgacc  1020
gtgagcagcc tgcaggaagc ggtgcaggcg gtgagcagcg atcaggaact gctgagccgc  1080
gtgaaaaaca tgcagaaaga tgtgaaagaa gcgggcggcg cggaacgcgc ggcggcggaa  1140
attgaagcgt ttatgaaaaa aagcgcggtg ccgcag                            1176

SEQ ID NO: 3                    moltype = DNA   length = 26
FEATURE                         Location/Qualifiers
source                          1..26
                                mol_type = other DNA
                                organism = unidentified
SEQUENCE: 3
ctgaatgttc cggttattat tctgtg                                        26

SEQ ID NO: 4                    moltype = DNA   length = 31
FEATURE                         Location/Qualifiers
source                          1..31
                                mol_type = other DNA
                                organism = unidentified
SEQUENCE: 4
gcagcggaat gagattttgc gcatcacggc c                                  31

SEQ ID NO: 5                    moltype = DNA   length = 31
FEATURE                         Location/Qualifiers
source                          1..31
                                mol_type = other DNA
                                organism = unidentified
SEQUENCE: 5
ccgggcacct accacatggt cgaaatccgc g                                  31

SEQ ID NO: 6                    moltype = DNA   length = 29
FEATURE                         Location/Qualifiers
source                          1..29
                                mol_type = other DNA
                                organism = unidentified
SEQUENCE: 6
tggtaggtgc ccggatagtc ttcataggc                                     29

SEQ ID NO: 7                    moltype = DNA   length = 26
FEATURE                         Location/Qualifiers
source                          1..26
                                mol_type = other DNA
```

```
                        organism = unidentified
SEQUENCE: 7
atgtccgcgg gcggcgccga cctttc                                              26

SEQ ID NO: 8            moltype = DNA   length = 29
FEATURE                 Location/Qualifiers
source                  1..29
                        mol_type = other DNA
                        organism = unidentified
SEQUENCE: 8
ccgcccgcgg acatgttggc gatgtcgtc                                           29
```

CONSTRUCTION METHOD AND APPLICATIONS OF GLYCOSYLTRANSFERASE BS-YJIC MUTANT

TECHNICAL FIELD

The disclosure relates to the field of genetic engineering technologies, and more particularly to a glycosyltransferase BS-YjiC mutant, a construction method of the glycosyltransferase BS-YjiC mutant, and an application of the glycosyltransferase BS-YjiC mutant.

STATEMENT REGARDING SEQUENCE LISTING

The sequence listing associated with this application is provided in text format in lieu of a paper copy and is hereby incorporated by reference into the specification. The name of the XML file containing the sequence listing is 24024TBYX-USP1-SL.xml. The XML file is 9,517 bytes; is created on Mar. 22, 2024; and is being submitted electronically via patent center.

BACKGROUND

Ginsenoside is an important active ingredient in precious Chinese herbal medicines such as ginseng (also referred to as *Panax ginseng* C. A. Mey.), San Qi (also referred to as *Panax notoginseng* (Burkill) F. H. Chen ex C. H. Chow) and American ginseng (also referred to as *Panax quiquefolium* L.). At present, at least 289 kinds of ginsenosides have been identified. Ginsenosides have various structures, and generally have activities of improving cardiovascular and cerebrovascular diseases, immune system, nervous system and anti-tumor. According to different skeletons of ginsenoside aglycones, the ginsenosides can be divided into olcanane-type ginsenosides and dammarane-type ginsenosides. The main aglycones of the dammarane ginsenoside are protopanaxadiol (PPD), protopanaxatriol (PPT) and pseudo-ginsenoside, while oleanolic acid is the aglycone of the oleanane ginsenoside.

Glycosylation is an essential modification reaction in the biosynthesis of natural products, which can enhance the solubility, bioavailability, stability and biological activity of substrates by forming a variety of natural glucosides. BS-YjiC from *Bacillus subtilis* 168 is a hybrid and powerful uridine diphosphate-glucuronosyltransferase (UGT), which can not only efficiently catalyze C3-OH and C12-OH of PPD to synthesize rare ginsenosides F12 and Rh2, but also glycosylate at C3-OH, C6-OH and C12-OH sites of PPT to generate ginsenoside Rh1 and four unnatural ginsenosides. Therefore, the transformation of glycosyltransferase BS-YjiC is an effective method for industrial production of rare ginsenosides, which has a good application prospect. However, BS-YjiC has some defects, such as low stability, low thermal stability and low relative enzyme activity.

SUMMARY

In order to improve the stability, thermal stability and relative enzyme activity of glycosyltransferase, the disclosure provides a glycosyltransferase BS-YjiC mutant, and a construction method and an application thereof. Compared with the wild-type glycosyltransferase, the mutant provided by the disclosure is more suitable for catalyzing protopanaxadiol (PPD) to generate rare ginsenosides F12 and Rh2, and is more conducive to the flexibility of the production process.

The disclosure provides a glycosyltransferase BS-YjiC mutant, and the glycosyltransferase BS-YjiC mutant is one selected from the group consisting of: a K125I mutant, a K125I/N178I mutant, and a K125I/P313W mutant.

The K125I mutant is obtained by mutating lysine at the $15^{th}$ position of a glycosyltransferase BS-YjiC with the amino acid sequence as shown in SEQ ID NO: 1 into isoleucine.

The N178I mutant is obtained by mutating asparagine at the $178^{th}$ position of the glycosyltransferase BS-YjiC with the amino acid sequence as shown in SEQ ID NO: 1 into isoleucine.

The P313W mutant is obtained by mutating proline at the $313^{th}$ position of the glycosyltransferase BS-YjiC with the amino acid sequence as shown in SEQ ID NO: 1 into tryptophan.

The K125I/N178I mutant is obtained by mutating lysine at the $15^{th}$ position of the glycosyltransferase BS-YjiC with the amino acid sequence as shown in SEQ ID NO: 1 into isoleucine and simultaneously mutating asparagine at the $178^{th}$ position the glycosyltransferase BS-YjiC with the amino acid sequence as shown in SEQ ID NO: 1 into isoleucine.

The K125I/P313W mutant is obtained by mutating lysine at the $15^{th}$ position of the wild-type glycosyltransferase BS-YjiC with the amino acid sequence as shown in SEQ ID NO: 1 into isoleucine and simultaneously mutating proline at the $313^{th}$ position the wild-type glycosyltransferase BS-YjiC with the amino acid sequence as shown in SEQ ID NO: 1 into tryptophan.

The nucleotide sequence encoding the wild-type glycosyltransferase BS-YjiC is shown in SEQ ID NO: 2.

The disclosure also provides a construction method of the K125I/N178I mutant, which specifically includes the following steps:

S1, designing a primer K125I-F with the nucleotide sequence shown in SEQ ID NO: 3, a primer K125I-R with the nucleotide sequence shown in SEQ ID NO: 4, a primer N178I-F with the nucleotide sequence shown in SEQ ID NO: 5, and a primer N178I-R with the nucleotide sequence shown in SEQ ID NO: 6;

S2, constructing a recombinant vector, including: synthesizing a wild-type glycosyltransferase BS-YjiC gene with the nucleotide sequence shown in SEQ ID NO: 2, and inserting the synthesized wild-type glycosyltransferase BS-YjiC gene into BamH I and Sal I sites of a vector pET-28a(+) to obtain the recombinant vector pET-28a(+)-YjiC;

S3, obtaining a recombinant plasmid containing a mutant gene, including: performing site-directed mutation by using the recombinant vector pET-28a(+)-YjiC obtained in the step S2 as a template and using the primers in the step S1, obtaining the recombinant plasmid containing the mutant gene as pET-28a(+)-YjiC-K125I/N178I; and S4, transferring the recombinant plasmid containing the mutant gene pET-28a(+)-YjiC-K125I/N178I into *Escherichia coli* competent cells to obtain the K125I/N178I mutant.

In an embodiment, in the step S3, a process of the site-directed mutation of the recombinant plasmid is as follows: taking the recombinant vector pET-28a(+)-YjiC as the template and the primer K125I-F and the primer K125I-R in the step S1 as the primers, and performing polymerase chain reaction (PCR) amplification to obtain a recombinant plasmid pET-28a(+)-YjiC-K125I; and then taking the recombinant plasmid pET-28a(+)-YjiC-K125I as a template, taking the primer N178I-F and the primer N178I-R obtained in the step S1 as the primers, performing PCR amplification to obtain the recombinant plasmid containing the mutant gene pET-28a(+)-YjiC-K125I/N178I.

The disclosure also provides a construction method of the K125I/P313W mutant, which specifically includes the following steps:

S1, designing a primer K125I-F with the nucleotide sequence as shown in SEQ ID NO: 3, a primer K125I-R with a nucleotide sequence as shown in SEQ ID NO: 4, a primer P313W-F with the nucleotide sequence as shown in SEQ ID NO: 7, and a primer P313W-R with the nucleotide sequence as shown in SEQ ID NO: 8;

S2, constructing a recombinant vector, including: synthesizing a wild-type glycosyltransferase BS-YjiC gene, inserting the wild-type glycosyltransferase BS-YjiC gene into BamH I and Sal I sites of a vector pET-28a(+) to obtain the recombinant vector pET-28a(+)-YjiC;

S3, obtaining a recombinant plasmid containing a mutant gene, including: performing site-directed mutation by using the recombinant vector pET-28a(+)-YjiC as a template to obtain the recombinant plasmid containing the mutant gene pET-28a(+)-YjiC-K125I/P313W; and S4, transforming the recombinant plasmid containing the mutant gene pET-28a(+)-YjiC-K125I/P313W into *Escherichia coli* competent cells to obtain the K125I/P313W mutant.

In an embodiment, in the step S3, a process of the site-directed mutation of the recombinant plasmid is as follows: taking the recombinant vector pET-28a(+)-YjiC as the template and the primer K125I-F and the primer K125I-R in the step S1 as the primers, performing PCR amplification to obtain a recombinant plasmid pET-28a(+)-YjiC-K125I; and then taking the recombinant plasmid pET-28a(+)-YjiC-K125I as a template and the primer P313W-F and the primer P313W-R as the primers, performing PCR amplification to obtain the recombinant plasmid containing the mutant gene pET-28a(+)-YjiC-K125I/P313W.

The disclosure also provides a gene encoding the glycosyltransferase BS-YjiC mutant.

The disclosure also provides a recombinant expression vector carrying the gene of the glycosyltransferase BS-YjiC mutant, and the recombinant expression vector is one selected from the group consisting of pET-28a(+)-YjiC-K125I, pET-28a(+)-YjiC-N178I, pET-28a(+)-YjiC-P313W, pET-28a (+)-YjiC-K125I/N178I, and pET-28a (+)-YjiC-K125I/P313W.

The disclosure also provides an application of the recombinant expression vector in preparing ginsenosides.

The disclosure also provides an application of the glycosyltransferase BS-YjiC mutant in preparing the ginsenosides.

Compared with the related art, the disclosure has the beneficial effects as follows.

1. On the basis of natural glycosyltransferase BS-YjiC (i.e., wild-type glycosyltransferase BS-YjiC), the molecular structure of the wild-type glycosyltransferase BS-YjiC is modified by rational design and site-directed mutation biotechnology, and the influence of mutated residues on the thermal stability of the enzyme is analyzed, and finally combined mutant strains (mutant strains K125I/N178I and K125I/P313W) with improved stability are obtained.

2. The melting temperature $T_m$ of the natural glycosyltransferase BS-YjiC is 47.30° C., and the melting temperature $T_m$ of the glycosyltransferase BS-YjiC mutant K125I/N178I provided by the disclosure reaches 54.51° C., which is 7.21° C. higher than that of the natural glycosyltransferase BS-YjiC. The melting temperature $T_m$ of the glycosyltransferase BS-YjiC mutant K125I/P313W reaches 53.07° C., which is 5.77° C. higher than that of the natural glycosyltransferase BS-YjiC.

3. The thermal stability of the glycosyltransferase BS-YjiC mutant provided by the disclosure is significantly improved, while the activity of the glycosyltransferase BS-YjiC mutant is not affected. After heat treatment at 45° C. for 90 minutes (min), the relative enzyme activities of mutants K125I/N178I and K125I/P313W retain 98.3% and 95.1% respectively, while the control retains 84.6% of the relative enzyme activity.

4. Compared with the wild-type glycosyltransferase BS-YjiC, the glycosyltransferase BS-YjiC mutant obtained by the disclosure is more suitable for catalyzing PPD to synthesize the rare ginsenoside Rh2, which is more conducive to the flexibility of the production process.

BRIEF DESCRIPTION OF DRAWINGS

In order to describe embodiments of the disclosure or the technical scheme in the related art clearer, the drawings needed to be used in the description of the embodiments or the related art will be briefly introduced below. Apparently, the drawings in the following description are only some embodiments of the disclosure, and other drawings can be obtained according to these drawings without creative work for those skilled in the art.

DETAILED DESCRIPTION OF EMBODIMENTS

Figure 1:
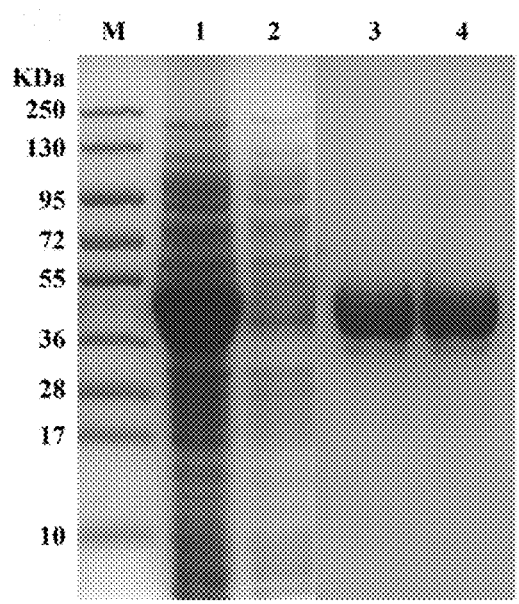
FIG. 1 illustrates analysis of pure enzyme solutions by sodium dodecyl sulfate-polyacrylamide gel electrophoresis (SDS-PAGE).

Hereinafter, specific embodiments of the disclosure will be described in detail, but it should be understood that the scope of protection of the disclosure is not limited by the specific embodiments. Based on the embodiments in the disclosure, all other embodiments obtained by those skilled in the art without creative work belong to the scope of protection of the disclosure. Unless otherwise specified, the experimental methods described in respective embodiments of the disclosure are all conventional methods, and the materials and reagents used in the following embodiments can be obtained from commercial sources unless otherwise specified.

In the following embodiments, the medium and formula involved are as follows:

1. Luria-Bertani (LB) liquid medium: 10 grams per liter (g/L) peptone, 5 g/L yeast powder, and 10 g/L sodium chloride (NaCl).

2. LB solid medium: 2% agar is added to the LB liquid medium.

The detection methods involved in the following embodiments are as follows.

1. Determination method of enzyme activity of glycosyltransferase BS-YjiC: 50 microliters (μL) of pure enzyme with a concentration of 1.5 milligrams per milliliter (mg/mL) is added to 950 μL of a reaction system containing 50 millimoles per liter (mM) Tris hydrochloride (Tris-HCl) (pH 8.0) buffer of 1 mM protopanaxadiol (PPD), 5 mM uridine diphosphate glucose (UDPG) and 8 mM magnesium chloride (MgCl2); reacted in a water bath at 35° C. for 30 minutes (min), then added the same volume of methanol to terminate the enzymatic reaction, so as to obtain a reacted product. The reacted product is centrifuged, then the supernatant is taken and filtered with a 0.22 micrometers (μm) filter to obtain a reaction solution, and the residual amount of PPD in the reaction solution is detected by high-performance liquid chromatography (HPLC).
2. Definition of enzyme activity: the amount of enzyme required to convert 1 micromole (μmol) of ginsenoside PPD per minute at 35° C. and pH 8.0 is defined as one unit of enzyme activity U.

Embodiment 1

K125I Mutant and Construction Method Thereof

S1, primers are designed.

Using the nucleotide sequence of wild-type glycosyltransferase BS-YjiC (as shown in SEQ ID NO: 2) as a template, point mutation primers K125I-F (as shown in SEQ ID NO: 3) and K125I-R (as shown in SEQ ID NO: 4) are designed. Specifically, the nucleotide sequences SEQ ID NO: 3 and SEQ ID NO: 4 are presented as follows:

```
SEQ ID NO: 3:
CTGAATGTTCCGGTTATTATTCTGTG;
and

SEQ ID NO: 4:
GCAGCGGAATGAGATTTTGCGCATCACGGCC.
```

S2, a recombinant vector containing the wild-type glycosyltransferase BS-YjiC is constructed.

The wild-type glycosyltransferase BS-YjiC gene with the nucleotide sequence as shown in SEQ ID NO: 2 is synthesized and inserted into BamH I and Sal I sites of a vector pET-28a(+) to obtain the recombinant vector pET-28a (+)-YjiC.

S3, a recombinant plasmid containing a mutant gene is obtained.

Using the whole plasmid PCR technique, the recombinant vector pET-28a(+)-YjiC prepared in the step S2 is used as a template for site-directed mutation, and the primers K125I-F and K125I-R in the step S1 are used as the primers for polymerase chain reaction (PCR) amplification to obtain the recombinant plasmid containing the mutant gene pET-28a(+)-YjiC-K125I.

Specifically, the PCR amplification program is set as follows: firstly, pre-denaturation at 95° C. for 5 min; then 30 cycles; denaturation at 95° C. for 30 seconds (s), annealing at 72° C. for 40 s, extension at 58° C. for 3.5 min, and heat preservation at 4° C. PCR products are detected by 0.8% agarose gel electrophoresis.

S4, the recombinant plasmid pET-28a(+)-YjiC-K125I is treated with Dpn I enzyme in a water bath at 37° C. for 1 hour (h) to remove the template, then transformed into *Escherichia coli* (*E. coli*) BL21 competent cells, to obtain a transformed solution. The transformed solution is coated on an LB solid medium containing kanamycin (50 micrograms per milliliter abbreviated as μg/mL), and the plasmid is extracted and sequenced. The sequencing work is completed by Sangon Biotech (Shanghai) Co., Ltd.

Embodiment 2

N178I Mutant and Construction Method Thereof

S1, primers are designed.

Using the nucleotide sequence of wild-type glycosyltransferase BS-YjiC (as shown in SEQ ID NO: 2) as a template, point mutation primers N178I-F (as shown in SEQ ID NO: 5) and N178I-R (as shown in SEQ ID NO: 6) are designed. Specifically, the nucleotide sequences SEQ ID NO: 5 and SEQ ID NO: 6 are presented as follows:

```
SEQ ID NO: 5:
CCGGGCACCTACCACATGGTCGAAATCCGCG;
and

SEQ ID NO: 6:
TGGTAGGTGCCCGGATAGTCTTCATAGGC.
```

S2, a recombinant vector containing the wild-type glycosyltransferase BS-YjiC is constructed.

The wild-type glycosyltransferase BS-YjiC gene with the nucleotide sequence as shown in SEQ ID NO: 2 is synthesized and inserted into BamH I and Sal I sites of a vector pET-28a(+) to obtain the recombinant vector pET-28a(+)-YjiC.

S3, a recombinant plasmid containing a mutant gene is obtained.

Using the whole plasmid PCR technique, the recombinant vector pET-28a(+)-YjiC prepared by the step S1 is used as a template, and the primers N178I-F and N178I-R are used as the primers for PCR amplification and site-directed mutation to obtain the recombinant plasmid containing the mutant gene pET-28a(+)-YjiC-N178I.

Specifically, the PCR amplification program is set as follows: firstly, pre-denaturation at 95° C. for 5 min; then 30 cycles; denaturation at 95° C. for 30 s, annealing at 72° C. for 40 s, extension at 58° C. for 3.5 min, and heat preservation at 4° C. PCR products are detected by 0.8% agarose gel electrophoresis.

S4, the recombinant plasmid pET-28a(+)-YjiC-N178I is treated with Dpn I enzyme in a water bath at 37° C. for 1 h to remove the template, then transformed into *E. coli* BL21 competent cells, to obtain a transformed solution. The transformed solution is coated on an LB solid medium containing kanamycin (50 μg/mL), and the plasmid is extracted and sequenced. The sequencing work is completed by Sangon Biotech (Shanghai) Co., Ltd.

Embodiment 3

P313W Mutant and Construction Method Thereof

S1, primers are designed.

Using the nucleotide sequence of wild-type glycosyltransferase BS-YjiC (as shown in SEQ ID NO: 2) as a template, point mutation primers P313W-F (as shown in SEQ ID NO:

7) and P313W-R (as shown in SEQ ID NO: 8) are designed. Specifically, the nucleotide sequences SEQ ID NO: 7 and SEQ ID NO: 8 are presented as follows:

```
SEQ ID NO: 7:
ATGTCCGCGGGCGGCGCCGACCTTTC;
and

SEQ ID NO: 8:
CCGCCCGCGGACATGTTGGCGATGTCGTC.
```

S2, a recombinant vector containing the wild-type glycosyltransferase BS-YjiC is constructed.

The wild-type glycosyltransferase BS-YjiC gene with the nucleotide sequence as shown in SEQ ID NO: 2 is synthesized and inserted into BamH I and Sal I sites of a vector pET-28a(+) to obtain the recombinant vector pET-28a(+)-YjiC.

S3, a recombinant plasmid containing a mutant gene is obtained.

Using the whole plasmid PCR technique, the recombinant vector pET-28a(+)-YjiC prepared by the step S1 is used as a template, and the primers P313W-F and P313W-R are used as the primers for PCR amplification and site-directed mutation to obtain the recombinant plasmid containing the mutant gene pET-28a(+)-YjiC-P313W.

Specifically, the PCR amplification program is set as follows: firstly, pre-denaturation at 95° C. for 5 min; then 30 cycles; denaturation at 95° C. for 30 s, annealing at 72° C. for 40 s, extension at 58° C. for 3.5 min, and heat preservation at 4° C. PCR products are detected by 0.8% agarose gel electrophoresis.

S4, the recombinant plasmid pET-28a(+)-YjiC-P313W is treated with Dpn I enzyme in a water bath at 37° C. for 1 h to remove the template, and then transformed into *E. coli* BL21 competent cells, to obtain a transformed solution. The transformation solution is coated on an LB solid medium containing kanamycin (50 μg/mL), and the plasmid is extracted and sequenced. The sequencing work is completed by Sangon Biotech (Shanghai) Co., Ltd.

Embodiment 4

K125I/N178I Mutant and Construction Method Thereof

S1, primers are designed.

Using the nucleotide sequence of wild-type glycosyltransferase BS-YjiC (as shown in SEQ ID NO: 2) as a template, point mutation primers K125I-F (nucleotide sequence as shown in SEQ ID NO: 3), K125I-R (nucleotide sequence as shown in SEQ ID NO: 4), N178I-F (nucleotide sequence as shown in SEQ ID NO: 5), and N178I-R (nucleotide sequence as shown in SEQ ID NO: 6) are designed.

The amino acid sequence of the wild-type glycosyltransferase BS-YjiC is shown in SEQ ID NO: 1.

```
SEQ ID NO: 1:
MKKYHISMINIPAYGHVNPTLALVEKLCEKGHRVTYATTEEFAPAVQQA

GGEALIYHTSLNIDPKQIREMMEKNDAPLSLLKESLSILPQLEELYKDD

QPDLIIYDFVALAGKLFAEKLNVPVIKLCSSYAQNESFQLGNEDMLKKI

REAEAEFKAYLEQEKLPAVSFEQLAVPEALNIVFMPKSFQIQHETFDDR

FCFVGPSLGERKEKESLLIDKDDRPLMLISLGTAFNAWPEFYKMCIKAF

RDSSWQVIMSVGKTIDPESLEDIPANFTIRQSVPQLEVLEKADLFISHG

GMNSTMEAMNAGVPLVVIPQMYEQELTANRVDELGLGVYLPKEEVTVSS

LQEAVQAVSSDQELLSRVKNMQKDVKEAGGAERAAAEIEAFMKKSAVPQ

SEQ ID NO: 2:
ATGAAAAAATATCATATTAGCATGATTAACATTCCGGCGTATGGCCATG

TGAACCCGACCCTGGCGCTGGTGGAAAAACTGTGCGAAAAAGGCCATCG

CGTGACCTATGCGACCACCGAAGAATTTGCGCCGGCGGTGCAGCAGGCG

GGCGGCGAAGCGCTGATTTATCATACCAGCCTGAACATTGATCCGAAAC

AGATTCGCGAAATGATGGAAAAAAACGATGCGCCGCTGAGCCTGCTGAA

AGAAAGCCTGAGCATTCTGCCGCAGCTGGAAGAACTGTATAAAGATGAT

CAGCCGGATCTGATTATTTATGATTTTGTGGCGCTGGCGGGCAAACTGT

TTGCGGAAAAACTGAACGTGCCGGTGATTAAACTGTGCAGCAGCTATGC

GCAGAACGAAAGCTTTCAGCTGGGCAACGAAGATATGCTGAAAAAAATT

CGCGAAGCGGAAGCGGAATTTAAAGCGTATCTGGAACAGGAAAAACTGC

CGGCGGTGAGCTTTGAACAGCTGGCGGTGCCGGAAGCGCTGAACATTGT

GTTTATGCCGAAAAGCTTTCAGATTCAGCATGAAACCTTTGATGATCGC

TTTTGCTTTGTGGGCCCGAGCCTGGGCGAACGCAAAGAAAAAGAAAGCC

TGCTGATTGATAAAGATGATCGCCCGCTGATGCTGATTAGCCTGGGCAC

CGCGTTTAACGCGTGGCCGGAATTTTATAAAATGTGCATTAAAGCGTTT

CGCGATAGCAGCTGGCAGGTGATTATGAGCGTGGGCAAAACCATTGATC

CGGAAAGCCTGGAAGATATTCCGGCGAACTTTACCATTCGCCAGAGCGT

GCCGCAGCTGGAAGTGCTGGAAAAAGCGGATCTGTTTATTAGCCATGGC

GGCATGAACAGCACCATGGAAGCGATGAACGCGGGCGTGCCGCTGGTGG

TGATTCCGCAGATGTATGAACAGGAACTGACCGCGAACCGCGTGGATGA

ACTGGGCCTGGGCGTGTATCTGCCGAAAGAAGAAGTGACCGTGAGCAGC

CTGCAGGAAGCGGTGCAGGCGGTGAGCAGCGATCAGGAACTGCTGAGCC

GCGTGAAAAACATGCAGAAAGATGTGAAAGAAGCGGGCGGCGCGGAACG

CGCGGCGGCGGAAATTGAAGCGTTTATGAAAAAAGCGCGGTGCCGCAG

SEQ ID NO: 3:
CTGAATGTTCCGGTTATTATTCTGTG

SEQ ID NO: 4:
GCAGCGGAATGAGATTTTGCGCATCACGGCC

SEQ ID NO: 5:
CCGGGCACCTACCACATGGTCGAAATCCGCG

SEQ ID NO: 6:
TGGTAGGTGCCCGGATAGTCTTCATAGGC
```

S2, a recombinant vector containing the wild-type glycosyltransferase BS-YjiC is constructed.

The wild-type glycosyltransferase BS-YjiC gene with the nucleotide sequence as shown in SEQ ID NO: 2 is synthesized and inserted into BamH I and Sal I sites of a vector pET-28a(+) to obtain the recombinant vector pET-28a(+)-YjiC.

S3, a recombinant plasmid containing a mutant gene is obtained.

Using the whole plasmid PCR technique, the recombinant vector pET-28a(+)-YjiC prepared by the step S1 is used as a template, and the primers K125I-F and K125I-R in the step S1 are used as primers for PCR amplification to obtain a recombinant plasmid pET-28a(+)-YjiC-K125I; and then the recombinant plasmid pET-28a(+)-YjiC-K125I is used as a template, the primers N178I-F and N178I-R obtained in the step S1 are used as primers for PCR amplification to obtain the recombinant plasmid containing the mutant gene pET-28a(+)-YjiC-K125I/N178I.

Specifically, the PCR amplification program is set as follows: firstly, pre-denaturation at 95° C. for 5 min; then 30 cycles; denaturation at 95° C. for 30 s, annealing at 72° C. for 40 s, extension at 58° C. for 3.5 min, and heat preservation at 4° C. PCR products are detected by 0.8% agarose gel electrophoresis.

S4, the recombinant plasmid pET-28a(+)-YjiC-K125I/N178I is treated with Dpn I enzyme in a water bath at 37° C. for 1 h to remove the template, then transformed into *E. coli* BL21 competent cells, to obtain a transformed solution. The transformation solution is coated on an LB solid medium containing kanamycin (50 μg/mL), and the plasmid is extracted and sequenced. The sequencing work is completed by Sangon Biotech (Shanghai) Co., Ltd.

Embodiment 5

K125I/P313W Mutant and Construction Method Thereof

S1, primers are designed.

Using the nucleotide sequence of wild-type glycosyltransferase BS-YjiC (as shown in SEQ ID NO: 2) as a template, point mutation primers K125I-F (as shown in SEQ ID NO: 3, and underlined bases indicate mutation sites), K125I-R (as shown in SEQ ID NO: 4), P313W-F (as shown in SEQ ID NO: 7), and P313W-R (as shown in SEQ ID NO: 8) are designed.

```
SEQ ID NO: 3:
CTGAATGTTCCGGTTATTATTCTGTG

SEQ ID NO: 4:
GCAGCGGAATGAGATTTTGCGCATCACGGCC

SEQ ID NO: 7:
ATGTCCGCGGGCGGCGCCGACCTTTC

SEQ ID NO: 8:
CCGCCCGCGGACATGTTGGCGATGTCGTC
```

S2, a recombinant vector containing the wild-type glycosyltransferase BS-YjiC is constructed.

The wild-type glycosyltransferase BS-YjiC gene with the nucleotide sequence as shown in SEQ ID NO: 2 is synthesized and inserted into BamH I and Sal I sites of a vector pET-28a(+) to obtain the recombinant vector pET-28a(+)-YjiC.

S3, a recombinant plasmid containing a mutant gene is obtained.

Using the whole plasmid PCR technique, the recombinant vector pET-28a(+)-YjiC prepared in the step S1 is used as a template, and the primers K125I-F and K125I-R in the step S1 are used as the primers for PCR amplification to obtain a recombinant plasmid pET-28a(+)-YjiC-K125I; and then the recombinant plasmid pET-28a(+)-YjiC-K125I is used as a template, the primers P313W-F and P313W-R are used as primers for PCR amplification to obtain the recombinant plasmid pET-28a(+)-YjiC-K125I/P313W.

Specifically, the PCR amplification program is set as follows: firstly, pre-denaturation at 95° C. for 5 min; then 30 cycles; denaturation at 95° C. for 30 s, annealing at 72° C. for 40 s, extension at 58° C. for 3.5 min, and heat preservation at 4° C. PCR products are detected by 0.8% agarose gel electrophoresis.

S4, the recombinant plasmid pET-28a(+)-YjiC-K125I/P313W is treated with Dpn I enzyme in a water bath at 37° C. for 1 h to remove the template, then transformed into *E. coli* BL21 competent cells, to obtain a transformed solution. The transformed solution is coated on an LB solid medium containing kanamycin (50 μg/mL), and the plasmid is extracted and sequenced. The sequencing work is completed by Sangon Biotech (Shanghai) Co., Ltd.

Embodiment 6

Construction of recombinant *E. coli* engineering bacteria producing glycosyltransferase mutants, and expression, separation and purification of α-glucosidase are as follows.

1. The recombinant plasmids pET-28a(+)-YjiC-K125I, pET-28a(+)-YjiC-N178I, pET-28a(+)-YjiC-P313W, pET-28a(+)-YjiC-K125I/N178I, and pET-28a(+)-YjiC-K125I/P313W obtained in the embodiments 1-5 are respectively transformed into *E. coli* BL21 competent cells, and genetically engineered bacteria: *E. coli*/pET-28a(+)-YjiC-K125I, *E. coli*/pET-28a(+)-YjiC-N178I, *E. coli*/pET-28a(+)-YjiC-P313W, *E. coli*/pET-28a(+)-YjiC-K125I/N178I, and *E. coli*/pET-28a(+)-YjiC-K125I/P313W are respectively prepared.

2. The genetically engineered bacteria prepared in the step 1 are inoculated into 10 mL LB liquid medium containing 50 μg/mL kanamycin, and cultured overnight at 37° C. and 200 revolutions per minute (rpm) to prepare seed solutions respectively.

The prepared seed solutions each are transferred to 100 mL LB liquid medium containing 50 μg/mL kanamycin according to the inoculation amount of 2% (v/v), cultured at 37° C. and 200 rpm until the optical density at a wavelength 600 nanometers (OD600) is 0.6-0.9, added isopropylthio-β-galactoside (IPTG) with the final concentration of 1 mM, and continue to culture at 16° C. for 20 h to obtain fermentation solutions. The prepared fermentation solutions each are centrifuged at 12000 rpm and 4° C. for 15 min to obtain cell thalli, and the cells are re-suspended with 10 mL of 50 mM Tris-HCl buffer (pH 8.0) after being washed three times. The resuspended cells are treated with an ultrasonic crusher in an ice bath for 30 min, centrifuged for 30 min (8000×g, 4° C.), and the supernatants are taken to obtain crude enzyme solutions.

The supernatants each are filtered through a 0.22 μm filter, and then further loaded on a 1 mL Ni affinity column, which is pre-balanced with 50 mM washing buffer (20 mM Tris and 250 mM NaCl, pH 8.0), and then the unbound protein and glycosyltransferase BS-YjiC are linearly eluted with an elution buffer (20 Mm Tris, 250 Mm NaCl and 500 Mm imidazole, Ph 8.0). In this situation, a pure enzyme solution containing the wild-type glycosyltransferase BS-YjiC, a pure enzyme solution containing K125I, a pure enzyme solution containing N178I, a pure enzyme solution containing P313W, a pure enzyme solution containing K125I/N178I and a pure enzyme solution containing K125I/P313W are respectively prepared.

The above pure enzyme solutions are analyzed by sodium dodecyl sulfate-polyacrylamide gel electrophoresis (SDS-PAGE), as shown in FIG. 1. The results show that there is an obvious band at 45 kilodaltons (kDa), which proves that glycosyltransferase BS-YjiC is expressed.

I. In order to test the influence of site-directed mutation on thermal stability, the thermal stability experiment is carried out on the prepared pure enzymes, and the method is as follows.

After the prepared pure enzymes are incubated in a water bath at 45° C. for 90 min, 1 mL is taken, and the residual enzyme activity of the remaining enzymes is determined according to the enzyme activity determination method of the glycosyltransferase BS-YjiC, and the percentage of residual enzyme activity is obtained by taking the enzyme activity of the pure enzyme solution without high-temperature treatment as a blank control. The test results are shown in Table 1.

TABLE 1

Residual enzyme activities of different pure enzymes

| Enzyme | Residual enzyme activity (%) |
|---|---|
| WT | 84.71 |
| K125I | 91.05 |
| N178I | 87.42 |
| P313W | 89.48 |
| K125I/N178I | 98.25 |
| K125I/P313W | 95.43 |

It can be seen from Table 1 that the mutants K125I, N178I, P313W, K125I/N178I and K125I/P313W retain 91.05%, 87.42%, 89.48%, 98.25% and 95.43% of the relative enzyme activities respectively, while the wild-type enzyme (i.e., the wild-type glycosyltransferase BS-YjiC, WT) and other mutants only retain about 84.71%. The thermal stability of all mutants is higher than that of wild-type enzyme.

II. Initial enzyme activity of the pure enzyme solutions prepared above is determined.

The pure enzyme solutions containing the wild-type glycosyltransferase BS-YjiC, K125I, N178I, P313W, K125I/N178I, and K125I/P313W prepared above are detected respectively, and the results are shown in Table 2.

TABLE 2

Initial enzyme activities of different pure enzyme solutions

| Enzyme | Initial enzyme activity (%) |
|---|---|
| WT | 100 |
| K125I | 103.15 |
| N178I | 98.76 |
| P313W | 96.53 |
| K125I/N178I | 106.47 |
| K125I/P313W | 105.13 |

Embodiment 7

Enzymatic Properties of Glycosyltransferase BS-YjiC Mutants

1. Thermal Stability

The pure enzyme solutions containing wild-type glycosyltransferase BS-YjiC, K125I, N178I, P313W, K125I/N178I and K125I/P313W prepared in the step 2 of the embodiment 6 are taken, respectively, then put in a constant temperature water bath at 45° C., and sampled every 30 min. The residual enzyme activity of glycosyltransferase BS-YjiC is measured according to the enzyme activity determination method, and its thermal stability is compared. The test results are shown in FIG. 2.

Figure 2:
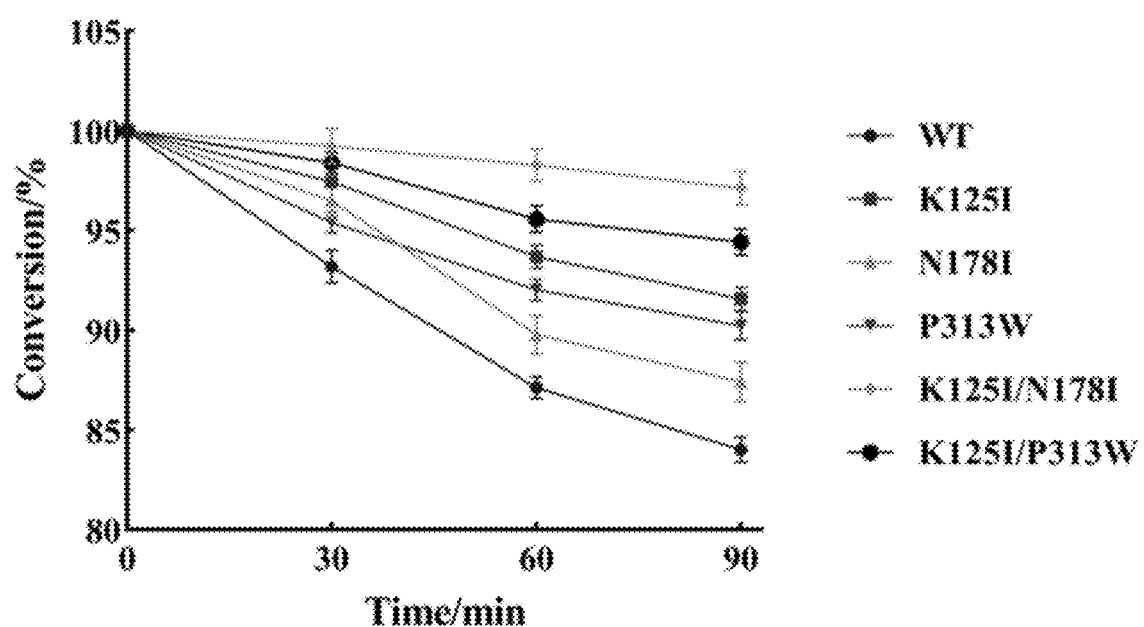
FIG. 2 illustrates test results of enzyme activity changes of a wild-type glycosyltransferase BS-YjiC (i.e., WT) and its mutants K125I, N178I, P313W, K125I/N178I and K125I/P313W incubated at 45° C. for different times.

It can be seen from FIG. 2 that the activity of the enzyme decreases with time, and the activity of single mutation and double mutation is higher than that of the non-mutation.

2. Kinetic Parameter 0.22 μg of pure enzyme is added into 50 mM Tris-HPLC (pH 8.0) buffer containing 10 mM UDPG and 8 mM MgCl2, added 50, 100, 200, 300, 400, 500, 600, 800 and 1000 μM PPD respectively, reacted at 35° C. in water bath for 30 min, and then then an equal volume of methanol is added to terminate the enzymatic reaction. The reacted products are centrifuged, then the supernatants are taken and filtered by a 0.22 μm filter to obtain reaction solutions, and the remaining amount of PPD in the reaction solutions is detected by HPLC. The results are shown in Table 3.

TABLE 3

Residual amount of protopanaxadiol PPD in reaction solutions

| Enzyme | $K_m$ (μM) | $V_{max}$ (U g$^{-1}$) | $K_{cat}$ (s$^{-1}$) | $k_{cat}/K_m$ (s$^{-1}$M$^{-1}$) |
|---|---|---|---|---|
| WT | 131.90 ± 32.12 | 8.32 ± 0.36 | 0.96 ± 0.06 | 0.72 × 10$^4$ |
| K125I | 127.90 ± 22.4 | 8.60 ± 0.41 | 0.99 ± 0.05 | 0.77 × 10$^4$ |
| N178I | 132.30 ± 33.82 | 8.75 ± 0.62 | 1.01 ± 0.07 | 0.76 × 10$^4$ |
| P313W | 136.40 ± 32 | 8.94 ± 0.60 | 1.11 ± 0.08 | 0.81 × 10$^4$ |
| K125I/N178I | 116.90 ± 22.49 | 8.82 ± 0.45 | 1.01 ± 0.05 | 0.87 × 10$^4$ |
| K125I/P313W | 120.80 ± 23.11 | 8.56 ± 0.44 | 0.98 ± 0.05 | 0.82 × 10$^4$ |

3. Optimum pH

The pure enzyme solutions containing the wild-type glycosyltransferase BS-YjiC, K125I/N178I, and K125I/P313W prepared in the step 2 of the embodiment 6 are placed in a 50 mM buffer containing sodium dihydrogen phosphate/disodium hydrogen phosphate (pH 6.5-7.5) and Tris-HCl (pH 7.5-8.5), and incubated for 1 h. The enzyme activities are measured by taking the initial enzyme activity without incubation as 100%. The results are shown in FIG. 3.

Figure 3:
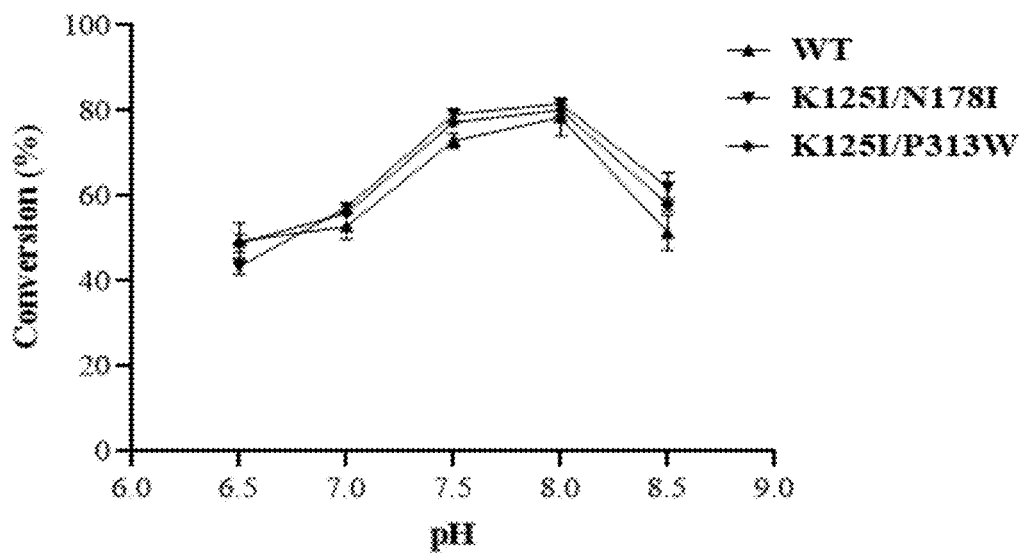
FIG. 3 illustrates test results of enzyme activities of the wild-type glycosyltransferase BS-YjiC and its mutants K125I/N178I and K125I/P313W at different pH values.

As can be seen from FIG. 3, the optimum pH of the mutant is 8.0, which is similar to that of the wild-type enzyme.

4. Optimum Temperature

The pure enzyme solutions containing the wild-type glycosyltransferase BS-YjiC, K125I/N178I, and K125I/P313W prepared in the step 2 of the embodiment 6 are placed in a buffer containing 50 mM Tris-HCl (pH 8.0), the reaction temperature is set at a range of 30° C. to 55° C., and the enzyme activities are determined taking the initial enzyme activity without incubation as 100%. The results are shown in FIG. 4.

Figure 4:
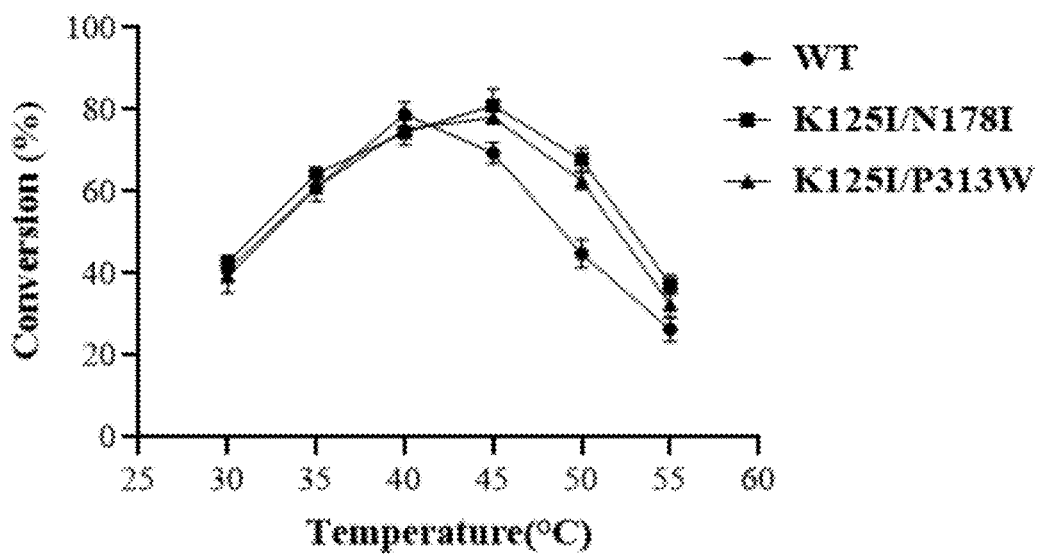
FIG. 4 illustrates test results of enzyme activities of the wild-type glycosyltransferase BS-YjiC and its mutants K125I/N178I and K125I/P313W at different temperatures.

As can be seen from FIG. 4, the optimum temperature of the mutant is 45° C., which is 5° C. higher than that of the wild-type enzyme.

Although the illustrated embodiments of the disclosure have been described, those skilled in the art can make additional changes and modifications to these embodiments once they know the basic inventive concepts. Therefore, the appended claims are intended to be interpreted as including the illustrated embodiment and all changes and modifications that fall within the scope of the disclosure.

Apparently, those skilled in the art can make various modifications and variations to the disclosure without departing from the spirit and scope of the disclosure. Thus, it is intended that the disclosure include these modifications and variations provided that they are within the scope of the claims and their equivalents.

What is claimed is:

1. A glycosyltransferase BS-YjiC mutant, wherein the glycosyltransferase BS-YjiC mutant is a K125I/N178I mutant, the K125I/N178I mutant is a mutant where lysine at the $125_{th}$ position of the glycosyltransferase BS-YjiC with the amino acid sequence as shown in SEQ ID NO: 1 is mutated into isoleucine and asparagine at the $178^{th}$ position of the glycosyltransferase BS-YjiC with the amino acid sequence as shown in SEQ ID NO: 1 is mutated into the isoleucine; wherein the glycosyltransferase BS-YjiC mutant is at least 90% identical to the sequence of SEQ ID NO: 1, and the nucleotide sequence encoding the glycosyltransferase BS-YjiC is shown in SEQ ID NO: 2.

* * * * *